(12) United States Patent
Angelescu et al.

(10) Patent No.: US 9,410,894 B2
(45) Date of Patent: Aug. 9, 2016

(54) MICROFLUIDIC DEVICE FOR ANALYZING A PRESSURIZED FLUID

(71) Applicants: CHAMBRE DE COMMERCE ET D'INDUSTRIE DE REGION PARIS ILE DE FRANCE (ESIEE PARIS), Noisy le Grand (FR); EFS SA, Montagny (FR)

(72) Inventors: Dan Eugen Angelescu, Le Perreux sur Marne (FR); Pierre Freyermuth, Pierre Benite (FR)

(73) Assignees: CHAMBRE DE COMMERCE ET DE L'INDUSTRIE DE PARIS AU TITRE DE SON ETABLISSEMENT, Noisy le Grand (FR); EPS SA, Montagny (FR)

( * ) Notice: Subject to any disclaimer, the term of this patent is extended or adjusted under 35 U.S.C. 154(b) by 1 day.

(21) Appl. No.: 14/251,324

(22) Filed: Apr. 11, 2014

(65) Prior Publication Data
US 2014/0219872 A1 Aug. 7, 2014

Related U.S. Application Data

(63) Continuation-in-part of application No. PCT/FR2012/051484, filed on Jun. 27, 2012.

(30) Foreign Application Priority Data

Oct. 13, 2011 (FR) ..................................... 11 59278

(51) Int. Cl.
*G01N 21/78* (2006.01)
*G01N 1/38* (2006.01)
(Continued)

(52) U.S. Cl.
CPC .............. *G01N 21/78* (2013.01); *G01N 1/2035* (2013.01); *G01N 15/1459* (2013.01); *B01D 61/18* (2013.01); *B01D 2321/2016* (2013.01);
(Continued)

(58) Field of Classification Search
CPC ............ B01D 2321/2016; B01D 61/18; B01L 2300/0627; B01L 2300/0681; B01L 2300/0864; B01L 2300/0877; B01L 2300/161; B01L 2400/0487; B01L 3/502715; B01L 3/50273; B01L 3/502784; G01N 15/14
See application file for complete search history.

(56) References Cited

U.S. PATENT DOCUMENTS 4,837,161 A 6/1989 Stevens et al.
6,007,235 A * 12/1999 Freud et al. ................... 366/136
(Continued)

OTHER PUBLICATIONS

Auroux et al., "Micro Total Analysis Systems. 2. Analytical Standard Operations and Applications," *Analytical Chemistry*, Jun. 15, 2002, vol. 74, No. 12, pp. 2637-2652.
(Continued)

*Primary Examiner* — Jennifer Wecker
(74) *Attorney, Agent, or Firm* — Oliff PLC

(57) ABSTRACT

The invention relates to a microfluidic sensor for analyzing a fluid which is in a pipe and which is under a first pressure. The sensor includes a mixer for mixing amount of fluid from the pipe with at least one amount of a reactant from at least one tank, and an analyzer for analyzing the resulting mixture. The sensor further includes a sampling channel for sampling an amount of the fluid in the pipe, in order to supply the fluid the mixer and to pressurize the at least one tank. According to the invention, an outlet of the analyzer is subjected to a second pressure that is lower than the first pressure in the pipe, such that the fluid passively moves from the pipe towards the analyzer via the mixer, as well as towards the tank.

17 Claims, 2 Drawing Sheets

(51) Int. Cl.
  *G01N 1/00* (2006.01)
  *G01N 1/10* (2006.01)
  *G01N 1/20* (2006.01)
  *G01N 1/22* (2006.01)
  *G01N 15/02* (2006.01)
  *B01L 3/00* (2006.01)
  *G01N 15/14* (2006.01)
  *B01D 61/18* (2006.01)

(52) U.S. Cl.
  CPC ........ *B01L3/50273* (2013.01); *B01L 3/502715* (2013.01); *B01L 3/502784* (2013.01); *B01L 2300/0627* (2013.01); *B01L 2300/0681* (2013.01); *B01L 2300/0864* (2013.01); *B01L 2300/0877* (2013.01); *B01L 2300/161* (2013.01); *B01L 2400/0487* (2013.01); *G01N 1/2042* (2013.01); *G01N 1/38* (2013.01); *G01N 15/1429* (2013.01)

(56) References Cited

U.S. PATENT DOCUMENTS

| | | | | |
|---|---|---|---|---|
| 6,286,376 | B1* | 9/2001 | Davidson et al. | 73/865.5 |
| 7,799,278 | B2 | 9/2010 | Salamitou et al. | |
| 2002/0028519 | A1* | 3/2002 | Yguerabide et al. | 436/518 |
| 2002/0041832 | A1 | 4/2002 | Duriez et al. | |
| 2002/0090650 | A1* | 7/2002 | Empedocles et al. | 435/7.1 |
| 2002/0187074 | A1 | 12/2002 | O'Connor et al. | |
| 2006/0008382 | A1* | 1/2006 | Salamitou et al. | 422/57 |
| 2006/0061760 | A1* | 3/2006 | Matsumoto et al. | 356/246 |
| 2007/0231213 | A1* | 10/2007 | Prabhu et al. | 422/100 |
| 2007/0242269 | A1 | 10/2007 | Trainer | |
| 2008/0094627 | A1 | 4/2008 | Oldham et al. | |
| 2008/0145275 | A1 | 6/2008 | Chen | |
| 2009/0016672 | A1 | 1/2009 | Schmidt et al. | |
| 2009/0266421 | A1* | 10/2009 | Linder et al. | 137/1 |
| 2010/0155577 | A1 | 6/2010 | Kiesel et al. | |
| 2010/0221816 | A1* | 9/2010 | Hanafusa et al. | 435/287.2 |
| 2010/0297754 | A1* | 11/2010 | Solli et al. | 435/325 |
| 2010/0304494 | A1* | 12/2010 | Tokhtuev et al. | 436/100 |
| 2011/0291025 | A1* | 12/2011 | Fortin et al. | 250/458.1 |
| 2011/0318774 | A1* | 12/2011 | Larsen | 435/29 |
| 2012/0196280 | A1* | 8/2012 | Karlsen et al. | 435/6.1 |

OTHER PUBLICATIONS

West et al., "Micro Total Analysis Systems: Latest Achievements," *Analytical Chemistry*, Jun. 15, 2008, vol. 80, No. 12, pp. 4403-4419.
Thorsen et al., "Microfluidic Large-Scale Integration," *Science*, Oct. 18, 2002, vol. 298, pp. 580-584.
Psaltis et al., "Developing optofluidic technology through the fusion of microfluidics and optics," *Nature*, Jul. 27, 2006, vol. 442, pp. 381-386.
Stone et al., "Microfluidics: Basic Issues, Applications, and Challenges," *AIChE Journal*, Jun. 2001, vol. 47, No. 6, pp. 1250-1254.
Ohno et al., "Microfluidics: Applications for analytical purposes in chemistry and biochemistry," *Electrophoresis*, 2008, vol. 29, pp. 4443-4453.
International Search Report issued in International Patent Application No. PCT/FR2012/051484 mailed Nov. 6, 2012.

* cited by examiner

MICROFLUIDIC DEVICE FOR ANALYZING A PRESSURIZED FLUID

This is a Continuation-in-Part of International Application No. PCT/FR2012/051484 filed Jun. 27, 2012, which claims the benefit of French Patent Application No. 1159278, filed Oct. 13, 2011. The disclosures of these prior applications are hereby incorporated by reference herein in their entirety.

The present invention relates to a microfluidic sensor for analyzing a fluid present in a pressure pipe.

It has a particularly interesting application in the field of continuous monitoring and analysis of drinking water quality in distribution systems, in water treatment plants or in machines or instruments used for water treatment and purification. But the present invention has a wider scope since it can be applied to the measurement of different physical or electrochemical parameters of a fluid present in a pressure pipe.

Online control of water quality has become a very important aspect, both for safety and for health reasons, and many efforts are directed towards the creation of apparatuses that can provide real-time access to data on water quality. Generally, the water industry is under cost pressures: controlling devices should be relatively inexpensive to manufacture, maintenance thereof should not involve highly intensive tasks for staff, and should be minimized. Naturally, solutions of sensors that can be monitored at a lower cost are favored, preferably by using wireless remote technologies. As maintenance has to be performed at spaced times, the sensors should therefore be autonomous for long time periods, which automatically reduces the number of available detection technologies.

A critical aspect of online control of water quality involves chlorine concentration measurements. Chlorine is used worldwide as a water purifier and disinfectant to prevent the spread of waterborne diseases, and its control, both in water treatment plants and at different points in the water distribution network, is very important to ensure, on the one hand, that the supplied water has a high and constant quality, and on the other hand, to be able to detect possible sources of contamination of the water network. The chlorine concentration, while recognized as the most relevant water quality parameter, is not controlled everywhere using the same methods. In particular, there are countries where regulations require that the total chlorine content—which includes both free chlorine and chlorine that has already reacted with organic compounds in an oxidation reaction—is controlled, and there are countries where only the free (or available) chlorine content has to be reported. Therefore, a sensor for the online control of the chlorine concentration needs to detect both types of chlorine if it has to be deployed worldwide.

Document U.S. Pat. No. 7,799,278 is known which describes a sensor comprising a submersible housing and a substrate being partly outside of the housing for recovering the fluid to be analyzed and transferring it to an analyzing means which is located inside the housing. In this document U.S. Pat. No. 7,799,278, the housing is completely immersed in the fluid to be measured. At least one reactant is at the same pressure as the fluid to be analyzed. In one case, a pump is provided for circulating the fluid from the substrate to the housing. The inlet and outlet ports are at the same pressure. The system provided in this document U.S. Pat. No. 7,799,278 is cumbersome, remains very invasive and involves several sealing constraints since it is completely submersible.

A purpose of the present invention is a microfluidic sensor having a high level of autonomy.

Another purpose of the invention is a microfluidic sensor with low reactant consumption.

It is still another purpose of the invention to provide a sensor that is minimally invasive with a high level of safety.

At least one of the aforementioned objectives is achieved with a microfluidic device for analyzing a fluid present in a pipe under a first pressure. This device comprises:

a mixer for mixing an amount of fluid coming from the pipe with at least one amount of a reactant coming from at least one tank, and an analyzer for analyzing the mixture thus constituted.

This device further comprises a sampling channel for drawing an amount of fluid in the pipe, for supplying the mixer and for pressurizing said at least one tank. Advantageously, an outlet port of the analyzer is subjected to a second pressure lower than the first pressure in the pipe, such that the fluid passively moves from the pipe, on the one hand, to the analyzer via the mixer, and on the other hand, to said at least one tank.

The device according to the invention may be a sensor in which the use of a pump for conveying the fluid is avoided. The pressure difference between the pressure in the pipe and the pressure at the outlet port is advantageously used so that the fluid is naturally "suctioned" from the pipe to the analyzer. Thus, it can be said that the device is passive. It consumes little power, which enables an autonomous in-situ operation over a long period. The device can be supplied with current via the sector or preferably by means of an internal battery connected at least to the analyzer and other organs to be controlled such as valves.

In particular, such a microfluidic device includes a miniaturized chemical reactant tank. This allows both to perform a reliable measurement using a small amount of chemical reactant and not requiring expensive maintenance. This device can thus be deployed in remote locations to perform a continuous measurement, for example of chlorine, or another chemical parameter. Using the system pressure as a source of pressure to push the fluid through micro channels, the proposed sensor provides a configuration that is inherently safe: there is no possibility to contaminate the water system, particularly with the chemical reactants. Indeed, the pipe according to the invention may be a pipe of the drinking water supply system for example, which is under pressure, the fluid moves in the sensor thanks to the difference in pressure between the environment to be monitored and the outside of the pipe. This environment outside the pipe may be advantageously the ambient atmosphere; said second pressure is then the atmospheric pressure. This configuration ensures that the chemical reactant cannot penetrate the water pipe thereby conferring an inherent safety to the sensor.

The sensor according to the invention is further remarkable by the fact that one can use a single sampling channel to supply both the reactant tank and the mixer. Thus, these two components (reactant tank and mixer) are subjected to the same pressure source.

According to an advantageous characteristic of the invention, the channel conveying the fluid towards the mixer and the channel conveying the reactant from the tank towards the mixer, are shaped, i.e. have a geometry or are sized, such that the mixture proportions between the fluid and the reactant are predetermined.

Particularly, the sizing of channels imposes a flow rate ratio between the channels supplying the mixer. Thus, the quantity of reactant to be used for a given quantity of fluid is precisely defined.

According to an advantageous feature of the invention, the device according to the invention comprises at least one first valve in a channel of the tank, and one second valve in an outlet channel leading to the outlet port of the analyzer. The first valve is disposed in the path containing the reactant tank, upstream or preferably downstream of this tank, i.e. in the channel connecting the tank to the rest of the reactant device. When disposed downstream, the first valve is located between the tank and the mixer. This first valve allows stopping the supply of reactant to the mixer. In this case, the fluid may flow from the pipe via the mixer up to an outlet port in order to achieve for example a reactant-free rinsing.

The second valve, positioned particularly at the outlet of the device, allows blocking the flow of fluid in the device which remains under pressure.

The device according to the invention may further comprise, in addition to or independently of the first and second valves, a third valve in the sampling channel to also control the flow in the sampling pipe. The third valve allows for example to avoid that the device remains constantly under the pressure of the pipe.

Preferably, the analyzer is an optical cell. Other types of analyzers may be used instead of or in conjunction with the optical cell.

It is also possible to use a flow meter, an electrochemical sensor, a mechanical sensor of the MEMS ("Microelectromechanical System") type, a conductivity sensor disposed for example on the sampling channel, or any other type of sensor or measurement system for the given liquid.

Using an optical cell as an analyzer, the microfluidic sensor described in the present invention is used according to the principle of a chemical reaction, particularly for the measurement of chlorine. The fluid, such as water for example, is mixed with the chemical reactant, such as for example diethyl-p-phenylenediamin or DPD, and is subjected to a change in color which intensity is related to the concentration of chlorine in the water. By performing a measurement of the optical absorption in an optical micro-module, at a wavelength corresponding to the maximum absorption of the DPD, the optical density of the mixture is calculated and the concentration of chlorine is deduced. Reactants are available for measuring total chlorine or simply free chlorine. Reactants are available for measuring other chemical parameters, such as pH, ionic content. Hence, the sensor according to the invention is not limited in any way to measure chlorine and may be easily adapted by those skilled in the art for the measurement of other chemical parameters by adapting, replacing or supplementing the optical cell and reactants used.

The measurement of the chemical parameter may be continuous or by spot measurements, each spot measurement involving an intelligent management of valves to power the analyzer, perform the measurement, rinse and switch to the standby mode where the fluid no longer flows.

According to one embodiment of the invention, the optical cell may comprise at least:
one filtered light source,
an optical cavity formed from a transparent material and conveying the mixture, as for example, a rectangular cavity, a transparent channel, a coil, or an otherwise shaped cavity allowing the light to pass through a liquid of known thickness, and
a broadband detector.

According to another embodiment, the optical cell may comprise at least:
one filtered light source,
means for guiding light from the source to an optical cavity of a microfluidic chip (as for example, a rectangular cavity, a transparent channel, a coil, or an otherwise shaped cavity allowing the light to pass through a liquid of known thickness), said cavity containing the mixture,
one broadband detector, and
means for guiding light from the microfluidic chip to the broadband detector.

In this case, means for guiding light may comprise one or a combination of the following elements:
an optical fiber,
a waveguide obtained by micro-fabrication, and
a liquid waveguide.

According to another embodiment, the optical cell may comprise at least:
one broadband light source,
one optical cavity (for example, a rectangular cavity, a transparent channel, a coil, or an otherwise shaped cavity allowing the light to pass through a liquid of known thickness) formed from a transparent material and conveying the mixture, and
one detector associated with a given filter.

It is thus possible to have several detectors, each associated with a given filter, for detecting a given parameter.

According to yet another embodiment, the optical cell may comprise at least:
one broadband light source,
one optical cavity (for example, a rectangular cavity, a transparent channel, a coil, or an otherwise shaped cavity allowing the light to pass through a liquid of known thickness) formed from a transparent material and conveying the mixture,
one monochromator, and
one broadband detector.

In this case, the monochromator allows selecting a specific wavelength for measuring a given parameter. This monochromator may be, in a non-limiting example, a diffraction grating, and/or a filter wheel.

With the device according to the invention, it is possible to advantageously implement multiple tanks of reactants associated or not with valves, in order to select one or a combination of reactants. Each channel containing a tank may be specifically sized for imposing a given flow. When the device includes several tanks, these may be disposed in parallel.

According to one embodiment of the invention, said at least one reactant tank is of the piston type. In this case, the reactant is pushed by the piston which is itself pushed by the fluid coming directly from the sampling channel.

According to one embodiment of the invention, said at least one reactant tank is of the flexible membrane or flexible bag types. In the same manner as above, the reactant is provisioned according to the pressure exerted by the fluid coming from the sampling channel.

Preferably, the mixer is a passive micromixer so that it is not supplied with electricity and hence does not consume energy. Several examples of such micromixers exist, for example those cited in the following references: P.-A. Auroux et al. Anal. Chem. 74, p. 2637 (2002) or West, Becker, Tombrink and Manz, Anal. Chem. 80, 4403 (2008).

According to an advantageous feature of the invention, the device may further comprise a discharge tank located at an outlet port of the analyzer. With the use of micro-fabrication processes, the microfluidic sensor according to the invention may include at least one miniaturized reactant tank. Thus, minute doses (ranging from a few nanoliters to a fraction of microliter) of chemical reactants are used for each measurement, which gives the sensor a large autonomy, and reduces costs due to the use of chemical reactants. In addition, with the use of small amounts of reactants and samples, the problem of evacuation of fluid collected during a measurement is minimized: measures can be performed for years with a relatively small discharge tank.

Preferably, the sampling channel includes an end that is inserted in the pipe in a sealed manner, the rest of the device being disposed outside of the pipe. This end has a port which draws the pressurized fluid. Advantageously, a filter in form of a grid, for example, is disposed at that port to prevent impurities from obstructing the sampling channel or the rest of the sensor.

Of course, the different features, embodiments and variants of the invention may be combined with each other in various combinations to the extent that they are not incompatible or mutually exclusive.

Other advantages and features of the invention will become apparent upon examining the detailed description of an embodiment which is in no way limiting, and the accompanying drawings, in which.

Although the invention is not limited thereto, we will now describe a microfluidic sensor for monitoring water quality. To this end, a water sample is taken passively from a pressurized pipe. This water sample is then mixed with a small amount of a chemical reactant, the mixture is then sent to an optical analyzer for the detection of chlorine, for example. The fluid path is called passive since it runs between a pressurized pipe towards an outlet port subjected to a pressure lower than that of the pipe, without using a pump. The outlet pressure is typically at atmospheric pressure.

A microfluidic sensor may comprise submillimeter channels, with diameters typically ranging from 10 to 100 micrometers. Such a sensor may integrate different types of actuators and sensors to create complex fluidic handling and detection systems (Thorsen et al., Science 298, 580 (2002), Psaltis et al., Nature, 442, 381 (2006)). Microfluidic systems have recently been used in a variety of applications, including biotechnology, pharmaceuticals and analytical chemistry (Stone and Kim, AIChE Journal, 47, 6, 1250 (2001), Ohno Tachikawa and Manz, Electrophoresis vol 29, p. 4443 (2008), West, Becker, Tombrink and Manz, Anal. Chem. 80, 4403 (2008)).

Figure 1:
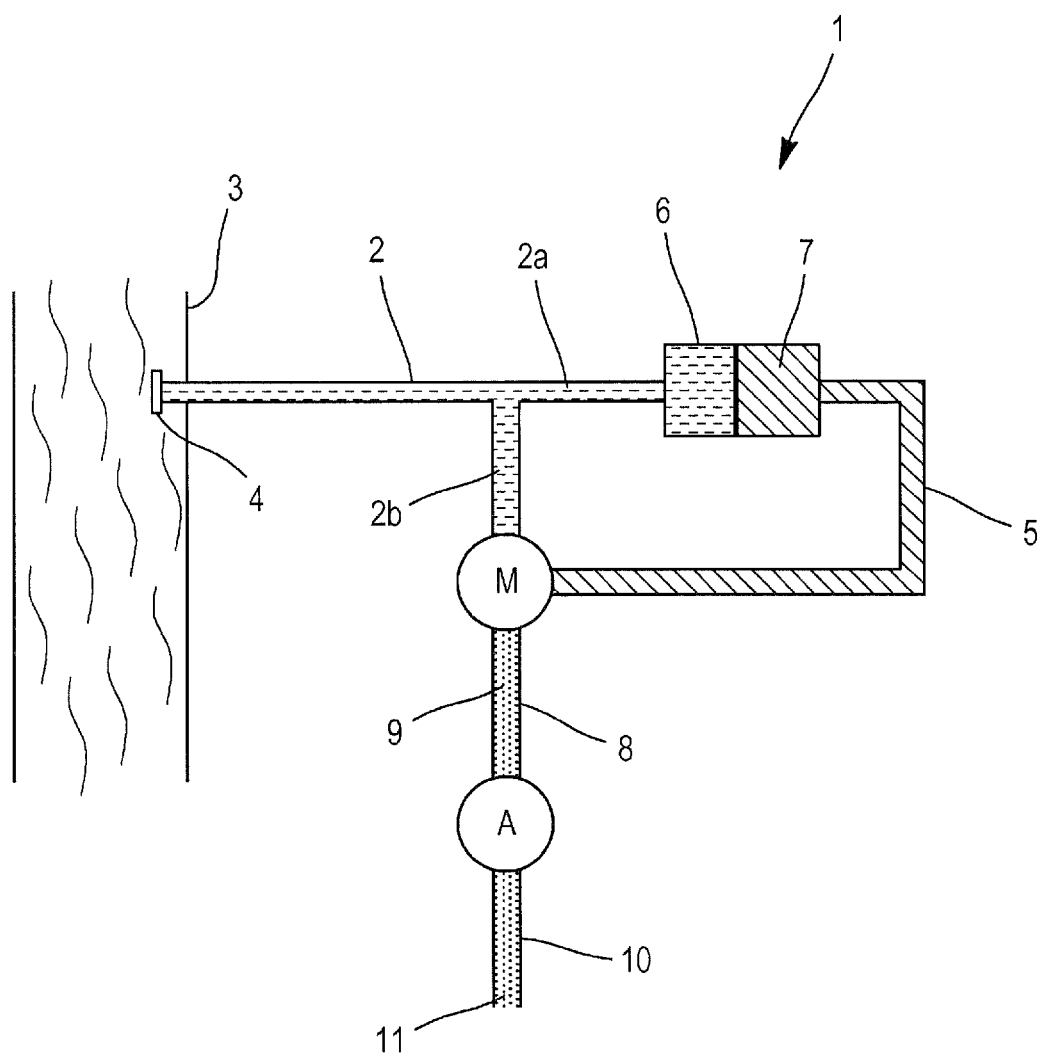
FIG. 1 is a schematic view illustrating the basic principle of a microfluidic sensor according to the invention.

FIG. 1 shows a microfluidic sensor 1 connected to a pipe 3 through which water flows under a pressure of 5 bars, for example. In general, it is a pipe supplying homes with drinking water. The pressurization of water allows a natural distribution in homes.

The microfluidic sensor 1 comprises a sampling channel 2 in which water from the pipe 3 flows. In the example shown in FIG. 1, there is one unique sampling channel 2 having a first end inserted in a sealed manner through the wall inside the pipe 3. The sampled water is filtered by means of a filter 4 before entering the microfluidic sensor, the filter being in the form of a grid or porous membrane, disposed on the orifice at the first end of the sampling channel 2. This avoids plugging the microfluidic channels.

Then, this sampling channel 2 directly supplies in parallel a passive mixer M and a tank 6. To do this, the channel 2 includes two arms, a first arm 2b supplying the passive mixer M, the second arm 2a supplying the tank 6.

The tank 6 is a tank containing a chemical reactant 7, such the DPD for chlorine detection. This tank comprises a piston or a flexible membrane or a sealed bag subjected to the pressure of water from the sample channel 2. With the microfluidic sensor according to the invention, the tank containing the chemical reactant 7 and the passive mixer M are subjected to a pressure, the source of which is unique: pipe 3.

Water and the chemical reactant 7 are combined in the passive mixer M. Water for the mixture is directly supplied through the sampling channel 2 and the arm 2b, while the chemical reactant is conveyed through a channel 5 disposed between the tank and the mixer M. The passive mixer M is a structure which ensures the mixing of different fluid inlets, resulting in a well-mixed fluid at the outlet. The concentration of the chemical reactant 7 may be controlled using hydraulic constrictions made in the channels 2b and 5, respectively. The fluid viscosity and the hydrodynamic resistance imposed by these constrictions define the flow rate of respective fluids via channels 2b and 5 respectively conveying water and the chemical reactant in the mixer M, the channel 2b being a branch of the channel 2 directly feeding the mixer M. The required concentration of the chemical reactant can be imposed and controlled by the design of channels. These constrictions consist of defining the geometry of the channels 2b and 5 so that the ratio between the proportion of water and the proportion of reactant used during a predetermined measurement. These constrictions may also be implemented inside the mixer M. The outlet of the mixer M is connected to a channel 8 conveying the mixture 9 that is the fluid from the mixture between water and the chemical reactant 7 in the mixer. This mixture 9 then enters an analyzer A particularly provided for detecting the presence of chlorine or other chemical product. This can be done, for example, by a colorimetric or spectroscopic measurement. It is possible that the mixer M and the analyzer A are made on the same microfluidic substrate, or on the same chip.

With the microfluidic sensor as shown in FIG. 1, it is possible to perform continuous measurements in situ in a manual or an automated fashion.

The outlet of the analyzer A is connected to a pipe 10, outlet port 11 of which is at atmospheric pressure, i.e. a pressure below the pressure present in the pipe. This pressure difference allows a passive flow (not pushed by active means such as a pump) from the sampling channel 2 to the outlet port 11. The water and/or chemical reactant flow in the channels 2, 2a, 2b, 5, 8 and 10. These channels communicate with each other directly or indirectly, so that a "string" or a pressure gradient between the filter 4 within the pipe and the outlet port 11, is created.

Figure 2:
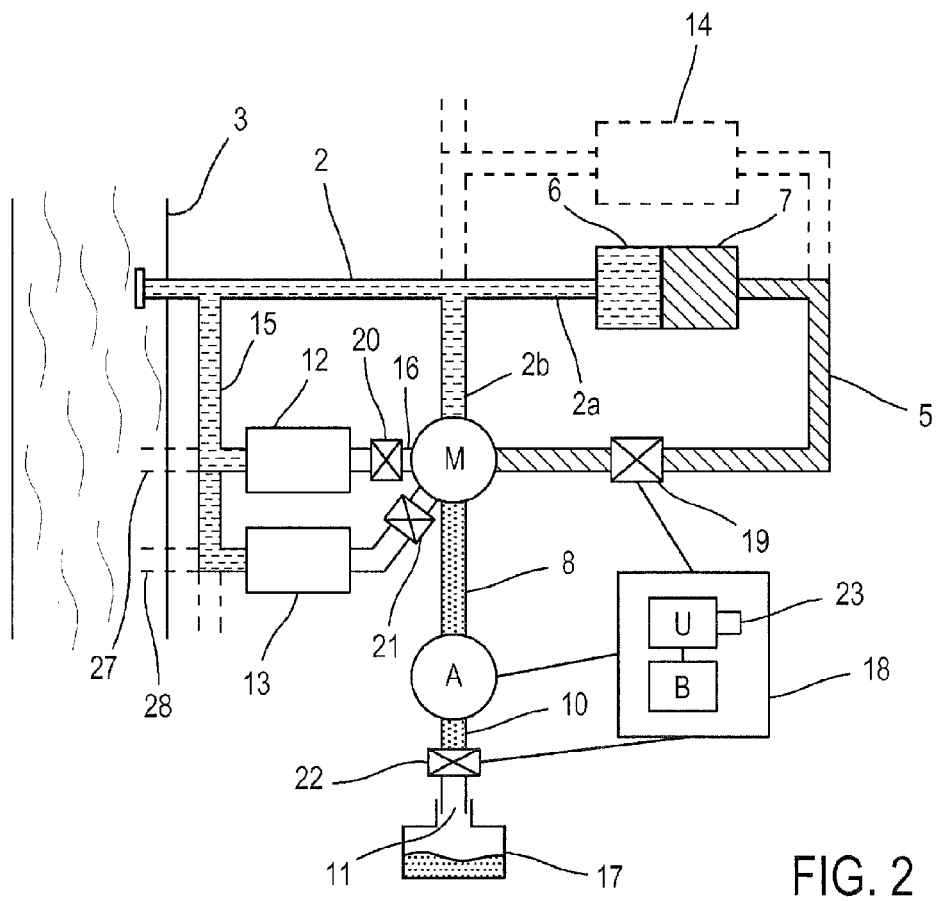
FIG. 2 is a schematic view illustrating a microfluidic sensor according to the invention showing an electronic module for controlling different electronic components.

In FIG. 2, each element already referenced in FIG. 1 and playing a similar role in both figures shows the same reference. There is a microfluidic sensor including more elements than the microfluidic sensor shown in FIG. 1. The sampling channel 2 supplies the mixer M and the tank 6, but it also supplies several other tanks in parallel to the tank 6. For example, a tank 12 including for example a chemical reactant which may be the same or different from the chemical reactant 7, can be seen. The sampling channel 2 includes an additional arm 15 to convey water from the pipe 3 to the tank 12. The latter is then connected to the mixer M via a channel 16, which may contain constrictions which serve to limit and/or control the flow rate of the chemical reactant between the tank 12 and the mixer M. In the same way as the tank 6, the tank 12 is also pressurized via the sampling channel 2. One can also provide other tanks such as the tank 13, shown in FIG. 2, also supplied with water via the sampling channel 2. This tank 13 may contain a cleaning agent such as an acid, for example. This acid can be used to clean the channels between the mixer and the analyzer until the outlet port 11. It may also have a multitude of tanks 13 disposed in parallel, supplying the mixer M independently.

As represented, the two tanks 12 and 13 are independently connected to the mixer M, the pressure of these tanks being established by channel 15 directly related to the pipe 2. However, there may be another tank 14 supplied directly by the sampling channel 2 and disposed parallel to tank 6, but not supplying independently (autonomously) the mixer M. In this embodiment, the tank 14 supplies the pipe 5 disposed between the tank 6 and the mixer M. The tank 14 may contain a chemical reactant identical or different from the chemical reactant 7 contained in the tank 6. It can also be a multitude of tanks 6 disposed in parallel, supplying the mixer M through the same pipe 5.

Additional tanks 12, 13 and 14 are optional and may be considered individually or in combination with each other. The channels connecting the reservoirs to the mixer M may also be dimensioned so as to predetermine the mixture proportions.

According to another advantageous embodiment of the invention, there is provided an independent fluid pressurization of the pipe of one or more additional tanks 12, 13 or 14. To do this, an independent pressurization consists of directly connecting the additional tank to the pipe 3 by means of another sampling channel different from the sampling channel 2. For example, the tank 12 and/or the tank 13 can be supplied directly, independently, by the pipe 3 as shown by the channels 27 and 28 in dashed lines in FIG. 2. Hence, the two tanks 12 and 13 are independently connected to the mixer M, the pressure of these tanks being established directly by pipe 3.

In FIG. 2, we distinguish an optional discharge tank 17 wherein the mixture used for the detection of chlorine is poured. This discharge tank also collects any fluid used during the cleaning of the channels. Due to the microfluidic nature of the sensor according to the invention, the volumes of reactants and water sample are very low, and autonomous operation can thus be ensured for extended periods.

The device of FIG. 2 is ideal for an autonomous and automatic operation. Particularly, there is a management module 18 comprising a power supply in form of a battery B (optionally, the management module may be powered by an external electrical power supply) and a processing unit U equipped with hardware and software means configured to control various electromechanical components of the microfluidic sensor. These software and hardware means may comprise a microprocessor and/or microcontroller. In particular, the management module 18 controls the optical analyzer A as well as micro valves 19, 20 and 21 respectively disposed on the channels between the mixer M and the tanks 6, 12 and 13. A micro valve 22 is also disposed on the outlet channel 10.

A measurement may be performed as follows. Valves 19 and 22 are opened so that water flowing from the pipe via the sampling channel 2 supplies the tank 6 which pushes the reactant 7 to the mixer M. Water also enters the mixer M directly via the sampling channel 2b. The mixture thus prepared supplies the analyzer A. Then, the valve 22 may be closed so as to perform a static measurement; this operation is suited for chemical reactants requiring a longer reaction time. If the valve 22 remains open, then a measurement is performed while the mixture flows into the analyzer A. At the end of the measurement, valves 19 and 20 may be closed until a subsequent measurement. It is also possible to envisage a cleaning of the mixer M at the end of the measurement or at another time. To do this, the valve 22 is opened if it has been closed or it is kept open if it has been opened, while closing the valve 19. In this case, water flows from the sampling channel 2 to the outlet port 11 via the mixer M and the analyzer A. Water is allowed to run long enough for all the residue of the reactant used previously drains. The valve 22 is then closed to return to an initial state.

During the measurement, it may be possible to open the valve 20 to add another reactant.

During cleaning, it may be possible to open the valve 21 to introduce a cleaning agent.

A valve (not shown) disposed on the sampling channel 2 on one of the arms directly supplying the mixer M or one of the water tanks, may be provided.

When a measurement is performed, the result may be saved internally within the management module 18 and/or transmitted by a wireline and/or wireless link to a remote receiver not shown. The processing unit U hence includes means of remote communication. The connector 23 may comprise an antenna for a wireless communication and/or a contact connector allowing transferring data to an external apparatus.

Figure 3:
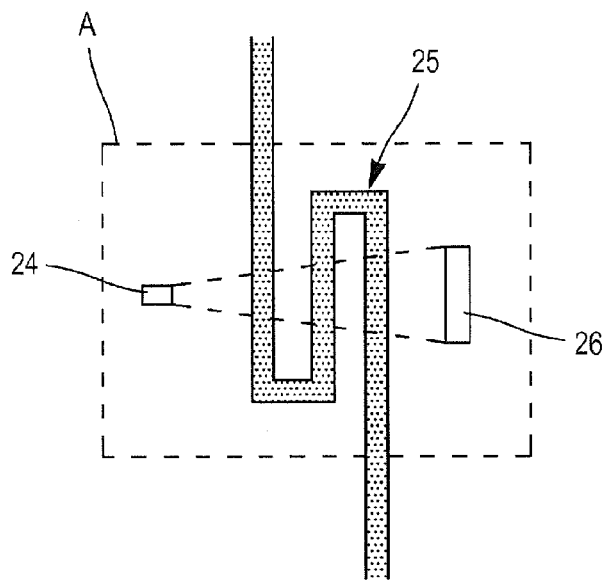
FIG. 3 is a schematic view illustrating an optical analyzer used in the microfluidic sensor according to the invention.

In FIG. 3, one distinguishes an optical analyzer consisting of a light source 24, a coil 25 filled with mixture from the mixer M and an optical detector 26. The coil is advantageously made in the continuity of the micro channel 8. Instead of the coil 25, any other optical cavity, rectangular for example, can be imagined. The light source and the detector may comprise optical filters which limit the spectrum of the light transmitted to some areas of interest of the optical spectrum. Typically, these optical filters restrict the wavelength of light to wavelengths where the chemical reactant (DPD for chlorine, for example) absorbs the most. Other optical filters may be used for the reference measurements at different wavelengths. These reference measurements may be used to eliminate the degradation of the sensor response due to possible changes in the optical path, or to the scattering of light by bubbles and/or particles.

The optical analyzer may also comprise other optical elements, such as lenses which provide good collimating light from the light source. Typical light sources produce a cone of light. Whenever such a cone of light passes through a narrow structure such as a micro-channel, most of the light hits the walls and is scattered or absorbed. Optical elements may be used to ensure that the light passes effectively through the portion of the channel containing the fluid to be measured. These optical elements (as non-limiting example of lenses, diaphragms, diffraction gratings, Bragg-type mirrors) may be built directly on-chip using micro-fabrication techniques, or may comprise external elements such as ball lenses, lensed fibers, diffraction gratings.

The microfluidic sensor according to the invention may also comprise other types of analyzers for performing measurements on the water sample. These may comprise, in a non-limiting example, measurements of electrical conductivity, amperometric measurements.

The advantages of the microfluidic sensor according to the invention are numerous, we can particularly mention:
 Reduced size,
 Reliable and standardized measurement,
 Low reactant consumption, low cost use and very high autonomy,
 Limited maintenance,
 Low cost calibration because the measurement is standardized,
 Can be deployed in remote locations to perform autonomously continuous chemical measurements over long periods, and
 Intrinsically safe configuration.

Of course, the invention is not limited to the examples described above and many modifications can be made to these examples without departing from the scope of the invention. For example, although microfluidic devices are exemplified, it will be readily understood and appreciated that the invention has equal applicability to other devices, including macrofluidic devices, microfluidic sensors, macrofluidic sensors, and the like.

The invention claimed is:

1. A microfluidic device for analyzing water present in a pipe under a first pressure, comprising:
   a sampling channel having a protruding upstream end configured to be sealingly inserted into the pipe and to draw water from the pipe, the rest of the microfluidic device being located outside of the pipe, a downstream portion of the sampling channel comprising:
   a first branch, and
   a second branch, a tank comprising:
   a water compartment in fluid connection with the second branch of the sampling channel,
   a reactant compartment configured to contain a volume of a chemical reactant, and
   a separator arranged between the water compartment and the reactant compartment, wherein said separator is selected from the group consisting of a piston, a flexible membrane, and a reactant flexible bag;
   a mixer in fluid connection with the first branch of the sampling channel, and in fluid connection with a conveying channel arranged to convey chemical reactant from the reactant compartment of the tank to the mixer, the mixer configured to receive an amount of the water from the second branch of the sampling channel and an amount of the reactant from the conveying channel, and to mix together the received water and the received chemical reactant to form a mixture, so that the chemical reactant can react with the water,
   an analyzer in fluid connection with the mixer and configured to receive and analyze the mixture from the mixer,
   wherein:
   the separator is configured to be displaceable by the water under a first pressure such that the water compartment is configured to pressurize the reactant compartment and passively move the chemical reactant from the reactant compartment to the mixer through the conveying channel without any pumping device, the microfluidic device having no pumping device, and
   the analyzer has a downstream outlet port configured to be subjected to a second pressure lower than the first pressure,
   the first branch and the second branch are arranged such that the water passively moves from the pipe towards the analyzer via the mixer, and also towards the tank, and
   the first and second branches are further respectively arranged such that the water compartment and the mixer are configured to be subjected to the first pressure.

2. The device of claim 1, wherein:
   the first branch includes a water hydraulic constriction,
   the conveying channel includes a reactant hydraulic constriction, and
   the water hydraulic constriction and the reactant hydraulic constriction are sized such that a mixture proportion between the water and the chemical reactant is predetermined.

3. The device of claim 1, further comprising a first valve in the conveying channel and a second valve in an outlet channel leading from the analyzer to the outlet port.

4. The device of claim 3, further comprising a third valve in the sampling channel for controlling the flow in the sampling channel.

5. The device of claim 1, wherein the analyzer is an optical cell comprising:
   a filtered light source,
   an optical cavity made from a transparent material and conveying the mixture, and
   a broadband detector.

6. The device of claim 1, wherein the analyzer is an optical cell comprising:
   a filtered light source,
   a first light guide configured to guide light from the filtered light source to an optical cavity of a microfluidic chip, the optical cavity configured to contain the mixture,
   a broadband detector, and
   a second light guide configured to guide light from the microfluidic chip to the broadband detector.

7. The device of claim 6, wherein the first and second light guides independently comprise one or a combination of the following elements:
   an optical fiber,
   a waveguide obtained by micro-fabrication, and
   a liquid waveguide.

8. The device of claim 1, wherein the analyzer is an optical cell comprising:
   a broadband light source,
   an optical cavity made from a transparent material and conveying the mixture, and
   a detector associated with a given filter.

9. The device of claim 1, wherein the analyzer is an optical cell comprising:
   a broadband light source,
   an optical cavity made from a transparent material and conveying the mixture,
   a monochromator, and
   a broadband detector.

10. The device of claim 1, wherein the mixer is a passive micromixer.

11. The device of claim 1, further comprising a discharge tank located at an outlet port of the analyzer.

12. The device of claim 1, wherein the second pressure is atmospheric pressure.

13. The device of claim 1, comprising a plurality of the tanks, the tanks being fluidically connected in parallel between the protruding upstream end and the mixer.

14. The device of claim 1, further comprising a cleaning tank configured to contain a cleaning agent, the cleaning tank being in fluid connection with the sampling channel and with the mixer.

15. The device of claim 1, wherein the analyzer is configured to analyze a chlorine content of the water.

16. The device of claim 1, wherein the pipe is a pipe of a drinking water supply system that is under pressure.

17. A microfluidic device for analyzing water present in a pipe under a first pressure, comprising:
   at least one tank configured to contain a chemical reactant,
   a mixer for mixing an amount of water coming from said pipe with at least one amount of said chemical reactant coming from said at least one tank, so that said chemical reactant can react with said water, an analyzer for analyzing the mixture thus constituted,
   wherein the microfluidic device further comprises a sampling channel configured for drawing by an extremity an amount of the water in the pipe at the first pressure, wherein the sampling channel is configured to supply in parallel said mixer and said at least one tank,
   the sampling channel comprising at least two arms including: a first arm for supplying said mixer and a second arm configured to pressurize said at least one tank in which a water volume coming from the sampling channel pushes said chemical reactant towards said mixer, said chemical reactant being conveyed in said mixer through a channel disposed between said at least one tank and said mixer;

wherein said at least one tank is configured to contain:

on the one hand, a water volume conveyed by the second arm, and on the other hand, the chemical reactant separated from the water volume and conveyed through a conveying channel disposed between said at least one tank and said mixer; and wherein an outlet port of said analyzer is subjected to a second pressure lower than said first pressure in said pipe, the second pressure being the pressure of the ambient atmosphere outside of the device, such that said water is configured to passively move from said pipe:

on the one hand towards and in said analyzer via said mixer, and on the other hand towards and in said at least one tank;

wherein said at least one tank and said mixer are subjected to a pressure, the source of which is unique, said source being said pipe, a pressure gradient between the sampling channel and the outlet port being created, the device being configured such that said water is not pushed by a pump.

* * * * *